(12) United States Patent
Yang et al.

(10) Patent No.: US 7,675,297 B1
(45) Date of Patent: Mar. 9, 2010

(54) METHODS FOR MEASURING BOUNDING CORROSION RATES USING COUPLED MULTIELECTRODE SENSORS AND ELIMINATING THE EFFECTS OF BAD ELECTRODES

(76) Inventors: Xiaodong Sun Yang, 11215 Jade Spring, San Antonio, TX (US) 78249; Lietai Yang, 11215 Jade Spring, San Antonio, TX (US) 78249

( * ) Notice: Subject to any disclaimer, the term of this patent is extended or adjusted under 35 U.S.C. 154(b) by 280 days.

(21) Appl. No.: 11/888,823

(22) Filed: Aug. 2, 2007

Related U.S. Application Data (60) Provisional application No. 60/835,331, filed on Aug. 3, 2006.

(51) Int. Cl.
G01R 27/08 (2006.01)
G01N 17/04 (2006.01)

(52) U.S. Cl. ............... 324/700; 324/71.2; 204/404; 205/775.5

(58) Field of Classification Search ............ 324/700, 324/71.2; 205/775.5
See application file for complete search history.

(56) References Cited

U.S. PATENT DOCUMENTS

| | | | |
|---|---|---|---|
| 4,667,150 A * | 5/1987 | Hausler et al. | 324/700 |
| 5,015,355 A * | 5/1991 | Schiessl | 204/404 |
| 6,132,593 A | 10/2000 | Tan | |
| 6,683,463 B2 | 1/2004 | Yang et al. | |
| 6,690,182 B2 * | 2/2004 | Kelly et al. | 324/700 |
| 6,987,396 B2 | 1/2006 | Yang et al. | |
| 7,180,309 B1 | 2/2007 | Yang | |

OTHER PUBLICATIONS

L. Yang and N. Sridhar, "Coupled Multielectrode Online Corrosion Sensor," Materials Performance, 2003, Septemeber issue, p. 48.
L. Yang, N. Sridhar, O. Pensado and D. Dunn, "An In-situ Galvanically Coupled Multi-Electrode Array Sensor for Localized Corrosion", Corrosion, 58, p. 1004, 2002.
Lietai Yang, Darrell Dun and Gustavo Cragnolino, "An Improved Method for Real-time and Online Corrosion Monitoring Using Coupled Multielectrode Array Sensors,".
Corrosion/2005, paper No. 05379, (Houston, TX: NACE International, 2005).
Xiaodong Sun and Lietai Yang, "Real-Time Monitoring of Localized and General Corrosion Rates in Simulated Marine Environments Using Coupled Multielectrode Array Sensors,".
Corrosion/2006, paper No. 06284 (Houston, TX: NACE, 2006).

* cited by examiner

*Primary Examiner*—Timothy J Dole
*Assistant Examiner*—John Zhu (57) ABSTRACT

The bounding corrosion rate is measured with a coupled multielectrode array sensor by decoupling a select number of anodic electrodes on the sensor from the coupling joint. In doing so, all or most of the electrons produced on the anodic electrode that remains connected to the coupling joint are forced to flow to the coupling joint and are thus measured. Because of the large number of electrodes on a multielectrode array sensor, one of them may become contaminated by foreign materials during the measurements or polishing process. The effect of such an electrode on the performance of the sensor can be eliminated by automatically disconnecting it from the coupling joint.

8 Claims, 11 Drawing Sheets

METHODS FOR MEASURING BOUNDING CORROSION RATES USING COUPLED MULTIELECTRODE SENSORS AND ELIMINATING THE EFFECTS OF BAD ELECTRODES

RELATED PATENT APPLICATION

This application claims the benefit of U.S. Provisional Application No. 60/835,331, filed Aug. 3, 2006, by Xiaodong Sun Yang and Lietai Yang, entitled "Methods for Measuring Bounding Localized Corrosion Rates Using Coupled Multielectrode Sensors and Eliminating the Effects of Bad Electrodes."

TECHNICAL FIELD OF THE INVENTION

This invention relates to methods for deriving localized corrosion parameters for corrosion monitoring, using multielectrode sensors.

BACKGROUND OF THE INVENTION

Coupled multielectrode array sensors (see U.S. Pat. No. 6,683,463, U.S. Pat. No. 6,132,593, and U.S. Pat. No. 7,180,309) have been used for corrosion monitoring and electrochemical studies (see L. Yang and N. Sridhar, "Coupled Multielectrode Online Corrosion Sensor," Materials Performance, 2003, September issue, page 48). The present invention is related to how to obtain a bounding localized corrosion rate using coupled multielectrode sensors, how to identify bad electrodes in a coupled multielectrode sensor, and how to eliminate the effects of such bad electrodes on the measurements of corrosion rates.

REFERENCE NUMBERS OF DRAWINGS 12 anodic or corroding area
13 bad anodic electrode or the false most corroding electrode
14 cathodic or non-corroding area
16 the most corroding or most anodic electrode (also called the true most anodic electrode)
18 the most cathodic electrode
20 insulator
22a electrode
22b electrode
24a multichannel ammeter or multiple ammeters or zero resistance ammeters
24b multichannel ammeter or multiple ammeters or zero resistance ammeters
26 coupling joint
30a resistor
30b resistor
32a multichannel voltmeter or multiple voltmeters
32b multichannel voltmeter or multiple voltmeters
40a switch
40b switch

DETAILED DESCRIPTIONS OF THE INVENTION

Overviews

Figure 1:
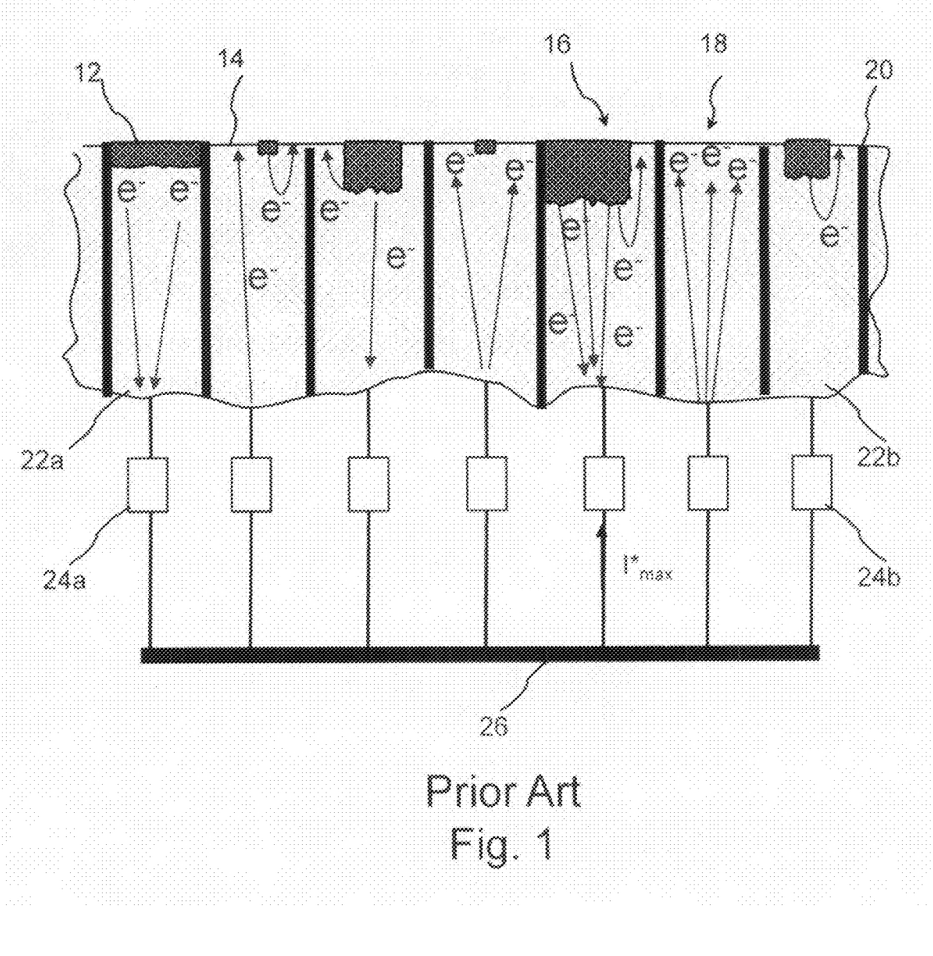
FIG. 1 illustrates typical wirings of a coupled multielectrode sensor, with ammeters or zero resistance ammeters, to measure the coupling current from each electrode to the coupling joint.
Figure 2:
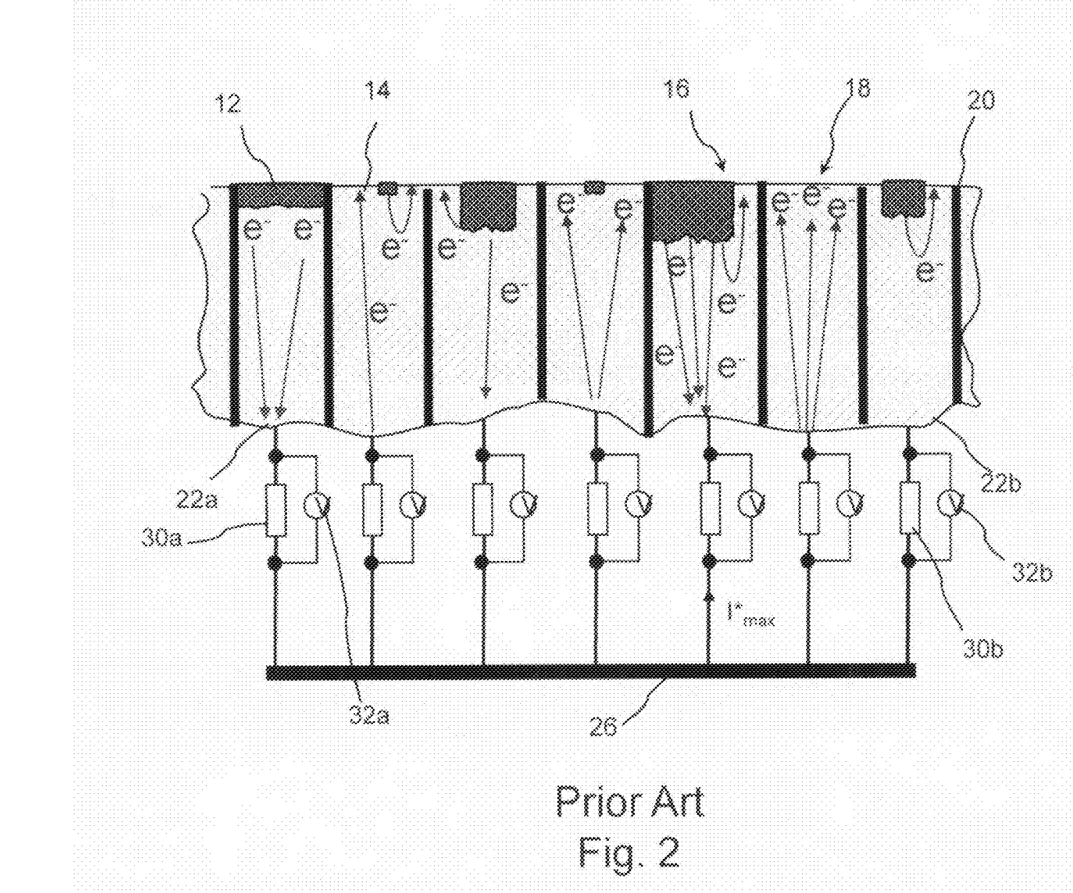
FIG. 2 illustrates typical wirings of a coupled multielectrode sensor, with resistors and voltage measuring units, to measure the coupling current from each electrode to the coupling joint.

FIGS. 1 and 2 show the principles of a coupled multielectrode sensor for localized corrosion measurements. The electrodes 22a or 22b of the sensor are made of substantially similar materials (such as wires, sheets, or rods). These electrodes are bundled together, with each electrode electrically insulated from the other electrodes by insulator 20. Each electrode is connected to a common joint, or coupling joint 26, via an ammeter (or a channel of a multichannel ammeter), a zero-resistance ammeter (24a or 24b in FIG. 1), or a resistor (30a or 30b in FIG. 2). The voltmeters or multichannel voltmeter 32a or 32b, in FIG. 2, are used to measure the voltage drops across the resistors, in order to derive the currents flowing though each electrode to the coupling joint 26. The electrodes 22a or 22b of a coupled multielectrode sensor are essentially at the same potential. Therefore, the electrodes simulate a one-piece metal electrochemically. In a localized corrosion environment, some of the electrodes are anodic (having more anodic area 12) and some electrodes are cathodic (having more cathodic area 14). The current from the most corroding electrode 16 (the electrode which has the highest anodic current, as shown in FIG. 1), $I^*_{max}$, or its statistical equivalent, has been used to derive the maximum localized corrosion rate (the maximum penetration rate), [see L. Yang, N. Sridhar, O. Pensado and D. Dunn, "An In-situ Galvanically Coupled Multi-Electrode Array Sensor for Localized Corrosion," Corrosion, 58, 1004, 2002; and L. Yang, D. Dunn and G. Cragnolino, "An Improved Method for Real-time and Online Corrosion Monitoring Using Coupled Multielectrode Array Sensors," CORROSION /2005, paper no. 05379, (Houston, Tex.: NACE International, 2005)]. The statistical equivalent may be defined as follows:

$$I^a{}_{max} = k\sigma + I_{mean} \quad (1)$$

Where k is a constant, $\sigma$ is the standard deviation of the measured currents, and $I_{mean}$ is the mean current. The value of k varies from 2 to 4, depending on the degree of confidence and the sample size (number of currents measured). The electrode that has the highest cathodic current is called the most cathodic electrode 18.

Because the surface area of the electrodes in a multielectrode probe is usually small (<0.01 cm$^2$), the corrosion on the most corroding electrode may be assumed to be uniform. Hence, localized corrosion rate (maximum penetration rate) may be calculated using the Faraday's Law:

$$CR_{max} = (1/\epsilon)(k\sigma + I_{mean})W_e/(F\rho A) \quad (2)$$

or $$CR^*{}_{max} = (1/\epsilon)(I^*{}_{max})W_e/(F\rho A) \quad (3)$$

Where $CR_{max}$ or $CR^*{}_{max}$ is the calculated maximum penetration rate (cm/s), $\epsilon$ is the current distribution factor (fraction of the electrons produced on the most corroding electrode that flow to the other electrodes through the coupling joint), F is the Faraday's constant (96485 C/mol), A is the surface area of the electrode (cm$^2$), $\rho$ is the density of the alloy or electrode (g/cm$^3$), and $W_e$ is the equivalent weight (g/mol).

The value of $\epsilon$ is close to unity, if the most corroding electrode is significantly different from the other electrodes in the coupled multielectrode sensor probe, and close to zero, if very few of the electrons flow to the other electrodes. In FIGS. 1 and 2, the value of $\epsilon$ is 0.75 (3 out of 4 electrons). Under conditions in which localized corrosion is not significant, the value of $\epsilon$ can vary and give uncertainties to the corrosion rate, calculated through use of Equations 2 or 3. To reduce this uncertainty, Yang et al. [see "An Improved Method for Real-time and Online Corrosion Monitoring Using Coupled Multielectrode Array Sensors," CORROSION/2005, paper no. 05379, (Houston, Tex.: NACE International, 2005)] proposed a method to force all the electrons produced on the most corroding electrode to flow externally, and thus to make $\epsilon = 1$. They achieved this result by applying an external power source to raise the potential of the coupling joint of the multielectrode sensor probe, such that the current from the most cathodic electrode would be close to zero. In this way, the coupling joint of the sensor is statistically at the highest potential of all reaction sites of the metal, if the sites can be separated from each other. At such a potential, no cathodic sites would be statistically available to receive the electrons produced on the most corroding electrode.

The drawback of the above potential-perturbation method, as described by Yang et al, is that it requires an external power source and an additional counter electrode to polarize the electrodes of the sensor. The external power source may also introduce additional noises to the system that needs to measure ultra-low level currents (close to 1 pA, in some cases) from the electrodes of a coupled multielectrode sensor probe. The present invention achieves the same purpose of forcing all electrons produced on the most corroding electrode to flow externally (to the coupling joint), without the need for an external power source or an additional electrode as a counter electrode.

By definition, coupled multielectrode sensors have many electrodes. Occasionally, one or more electrodes may become contaminated by highly active anodic species or highly active cathodic species. Such contamination would alter the behavior of the coupled multielectrode sensor probes. For example, a small piece of carbon steel may be stuck onto an electrode of a probe made of corrosion-resistant metals, such as Alloy 276, during polishing, if the polishing paper is not clean. Such a carbon steel piece will produce an exceptionally high anodic current flowing through the contaminated electrode (the bad electrode). Because the localized corrosion rate from the coupled multielectrode sensor probe is usually derived from the current flowing through the most corroding electrode (Equation 3) or the statistically most corroding electrodes, the high anodic current due to the dissolution of the carbon steel contamination would give a false and high corrosion rate. On the other hand, the contamination by the highly active carbon steel piece would lower the corrosion potential of the Alloy 276 probe and cause the anodic current flowing though the true most corroding electrode to be lower. Visa versa, if a small piece of material, which is highly catalytic for the reduction reaction of oxygen, is stuck on an electrode of the coupled multielectrode sensor probe, it would raise the corrosion potential of the sensor and cause the anodic current flowing through the most corroding electrode to be higher.

The present invention also describes a method for properly identifying the bad electrodes and eliminating the effect of such bad electrodes.

Bounding Corrosion Rate

Figure 3:
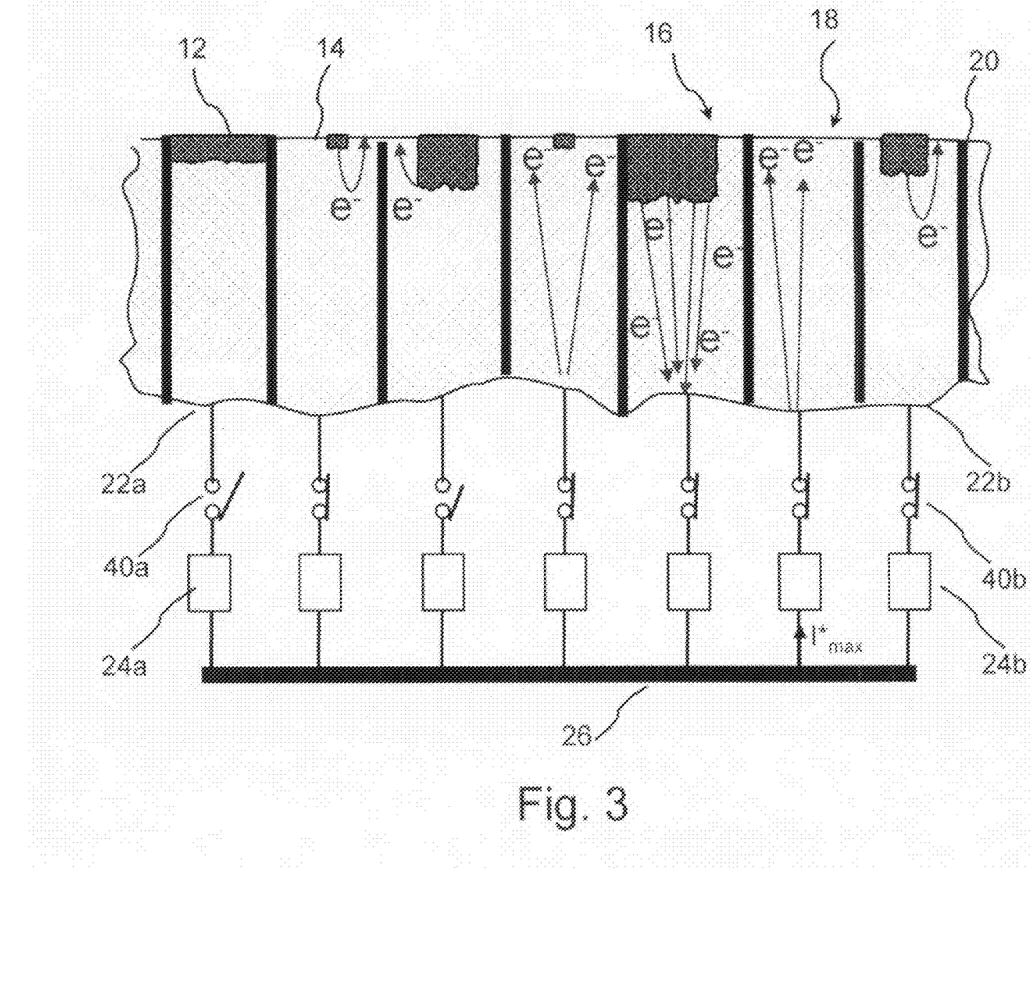
FIG. 3 illustrates the flow of electrons on the most corroding electrode, after all the electrodes that were initially anodic were disconnected from the coupling joint for a coupled multielectrode sensor with ammeters or zero resistance ammeters.
Figure 4:
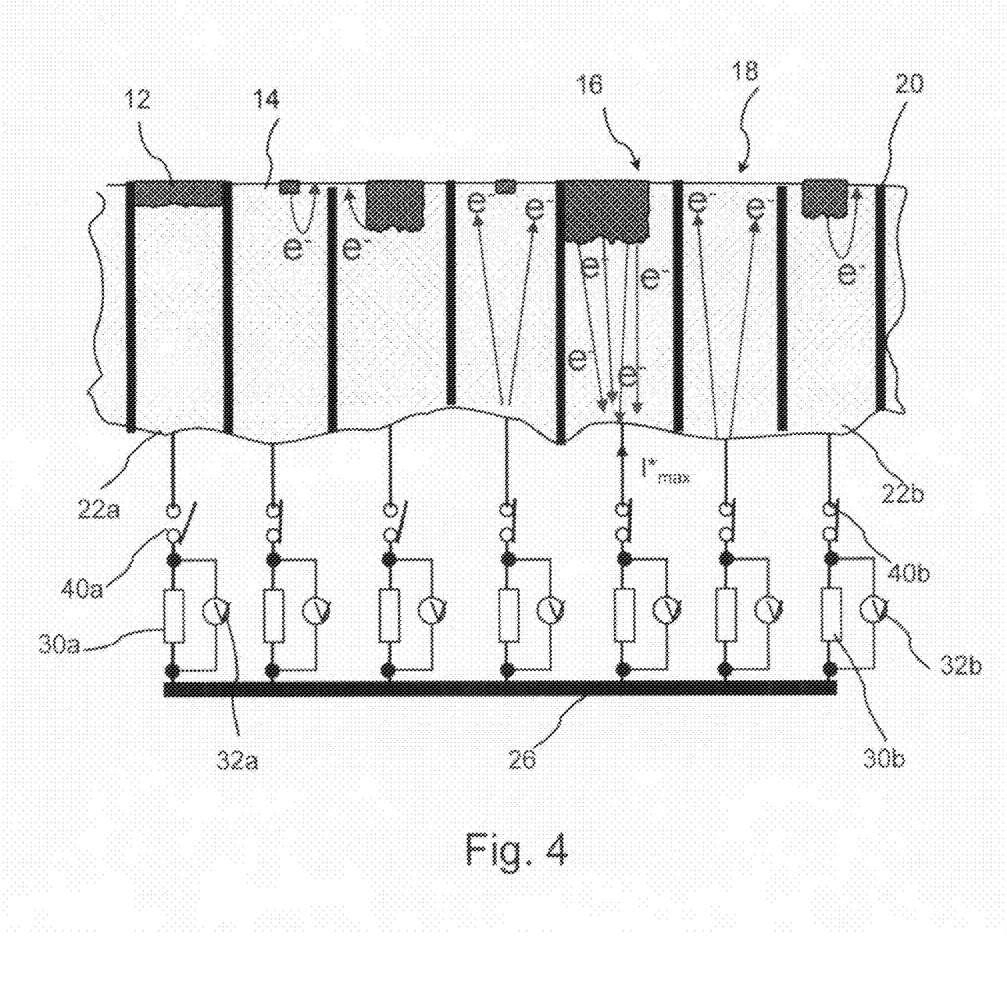
FIG. 4 illustrates the flow of electrons on the most corroding electrode, after all the electrodes that were initially anodic were disconnected from the coupling joint for a coupled multielectrode sensor with resistors and voltage measuring units.

FIGS. 3 and 4 show the embodiment of the present invention. A switch 40a or 40b is added between each electrode and the coupling joints in the circuits, as shown in FIGS. 1 and 2. With the addition of the switches, an operator—or an automated computer program—can disconnect some of the anodic electrodes so that only a few of the anodic electrodes (e.g., the most corroding electrode 16) remain coupled with all the cathodic electrodes. In this case, these electrodes (e.g., the most corroding electrode 16) are forced to be significantly more anodic than the rest of the electrodes in the coupling (the coupling potential of the sensor is raised). Therefore, all electrons produced on the most corroding electrode 16 would be more likely to flow externally to the other electrodes through the coupling joint. As shown in FIGS. 3 and 4, all 4 electrons produced on the most corroding electrode flow externally—no internal current on the most corroding electrode.

Figure 5:
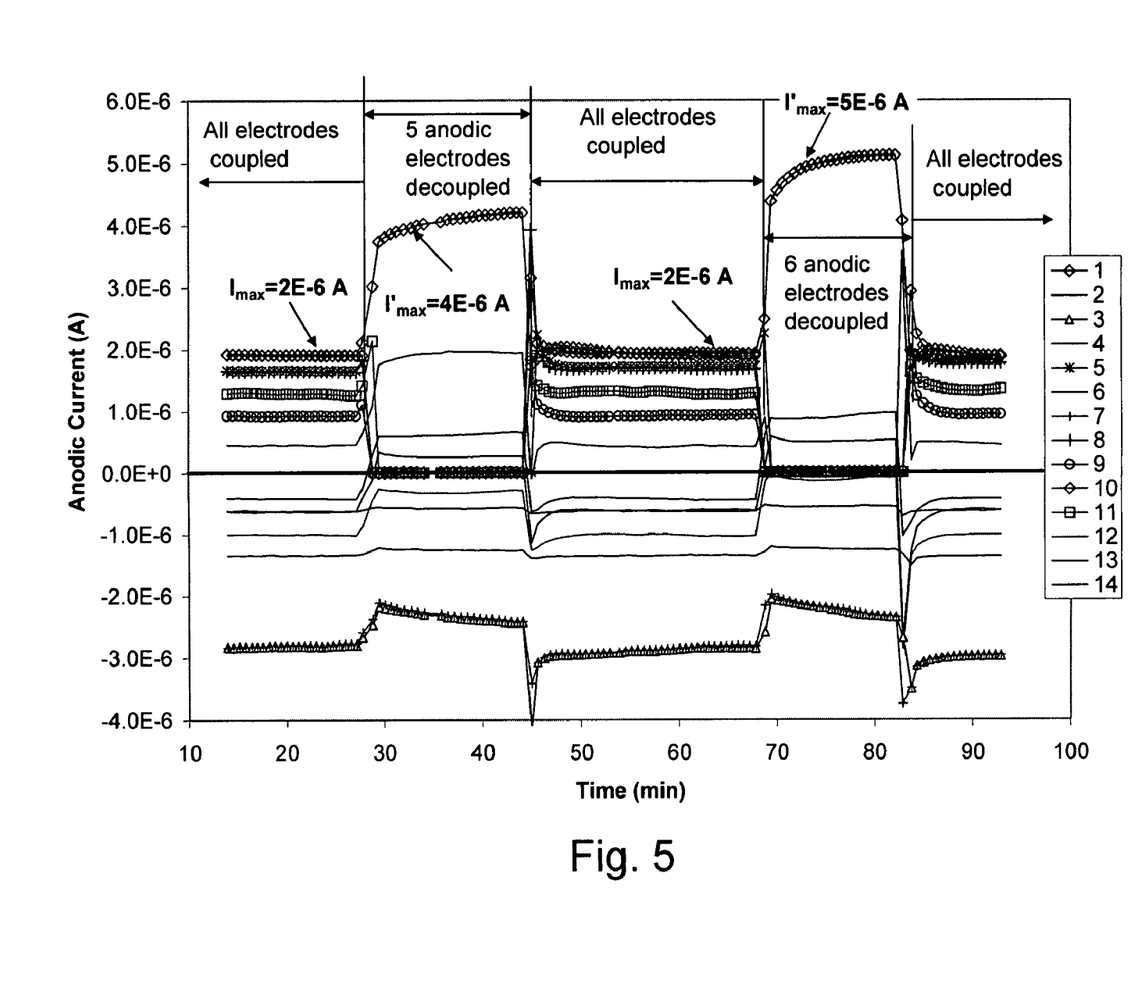
FIG. 5 illustrates the maximum anodic current before and after some anodic electrodes were removed from the coupling joint for a 14-electrode carbon steel probe in simulated seawater.
Figure 6:
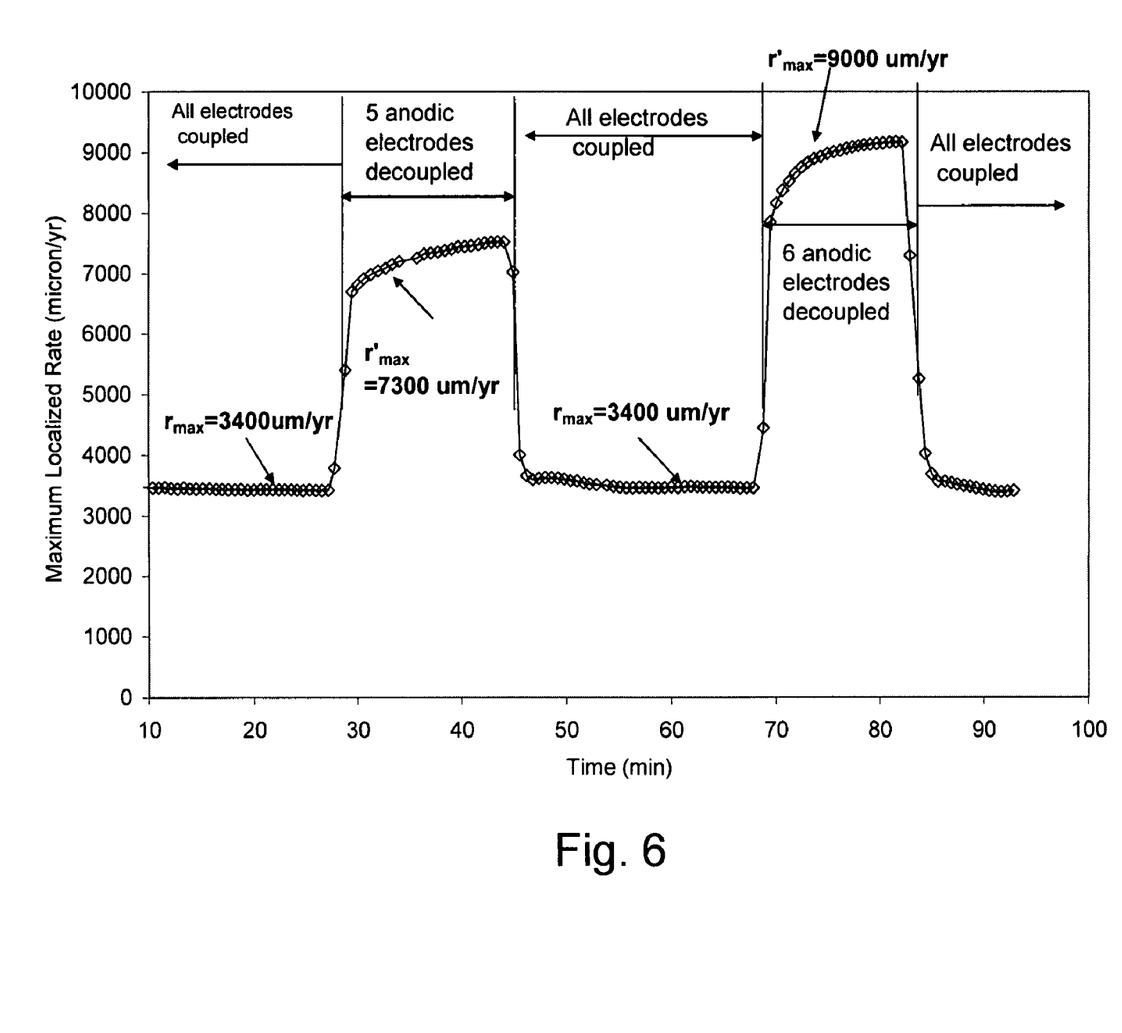
FIG. 6 illustrates the maximum localized corrosion rate with and without removing some anodic electrodes from the coupling joint, for the data shown in FIG. 5.

FIG. 5 shows the current from each electrode of a carbon steel probe immersed in simulated seawater, both with and without disconnecting (decoupling) some of the anodic electrodes. When some of the anodic electrodes were disconnected from the coupling joint, the anodic currents that are required to support the cathodic reactions at the cathodic electrodes were provided mainly by the most corroding electrode 16. Therefore, its current increased approximately 2 to 3 times. Because the most corroding electrode was so different from the other electrodes, the electrons produced on it would flow externally. In addition, the decoupling of the other anodic electrodes would cause the corrosion potential of the coupled multielectrode sensor probe to slightly shift positively, causing the most corroding electrode to polarize slightly. This polarization may initiate corrosion at the sites that would otherwise not have any corrosion. Therefore, the decoupling of some of the anodic electrodes may give a higher corrosion rate than the true corrosion rate on the electrodes that remain connected to the coupling joint. Nonetheless, the anodic current measured under this condition would be a bounding anodic current for the most corroding electrode and, therefore, it can be used to estimate the bounding maximum localized corrosion rate, as shown in FIG. 6. The corrosion rate ($r'_{max}$) derived with the other anodic electrodes decoupled is the bounding rate for the localized corrosion, which also includes the corrosion due to general corrosion.

Elimination of the Effect Caused by Bad Electrodes

As mentioned above, coupled multielectrode sensors have many electrodes. The inventors have occasionally found that one or more of them behave exceptionally different from others, due to contamination by highly active anodic species or highly active cathodic species, or due to the unusually high content of the impurities in one of the electrodes of the coupled multielectrode sensor probe. For example, a small piece of carbon steel may be stuck onto an electrode of a probe made of corrosion-resistant metals (such as Alloy 276) during polishing, if the polishing paper is not clean. Such a carbon steel piece will produce exceptionally high anodic current flowing through the contaminated electrode. Such a contaminated electrode is called the bad electrode or false most corroding electrode. Because the localized corrosion rate from the coupled multielectrode is usually derived from the current flowing through the electrode that has the highest anodic current, the high anodic current due to the dissolution of the carbon steel contamination would give a false high corrosion rate.

Figure 7:
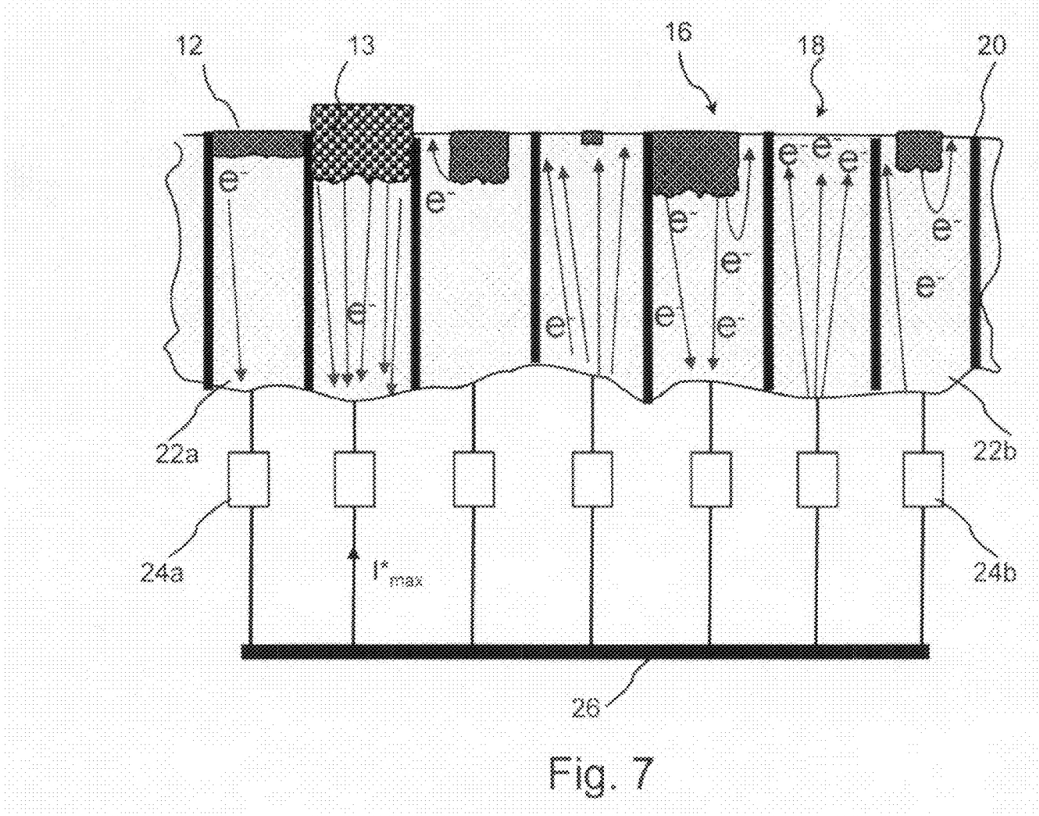
FIG. 7 illustrates a bad anodic electrode on a coupled multielectrode probe that may produce a false most corroding signal or reduce the current from the true 'most corroding' electrode.
Figure 8:
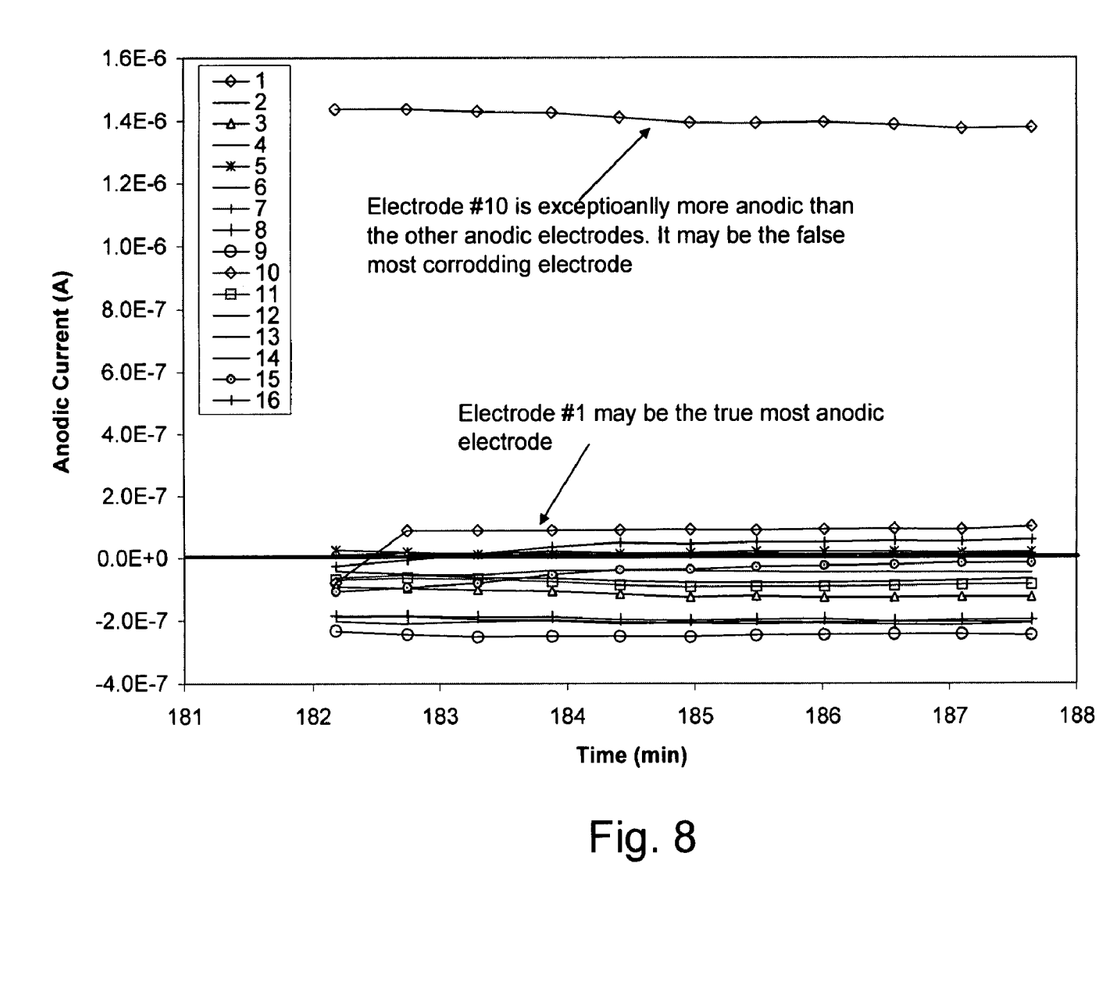
FIG. 8 illustrates a situation where one anodic electrode was a bad electrode statistically; such an electrode should be removed from the coupling joint, to assure reliable measurements.

On the other hand, the highly active carbon steel would lower the corrosion potential of the Alloy 276 probe and cause the anodic current flowing though the true most corroding electrode to be lower. FIG. 7 shows, schematically, how a bad anodic electrode or false most corroding electrode 13 would produce the false most corroding current. FIG. 8 shows an example case, observed by the inventors, where one electrode was significantly more anodic than the other electrodes. In FIG. 8, Electrode #10 was exceptionally more anodic than the other electrodes of the coupled multielectrode sensor probe. The true most corroding electrode may have been Electrode #1. But the anodic current flowing through Electrode #1 was extremely low, which may be caused by the lowering of the corrosion potential by Electrode #10.

Figure 9:
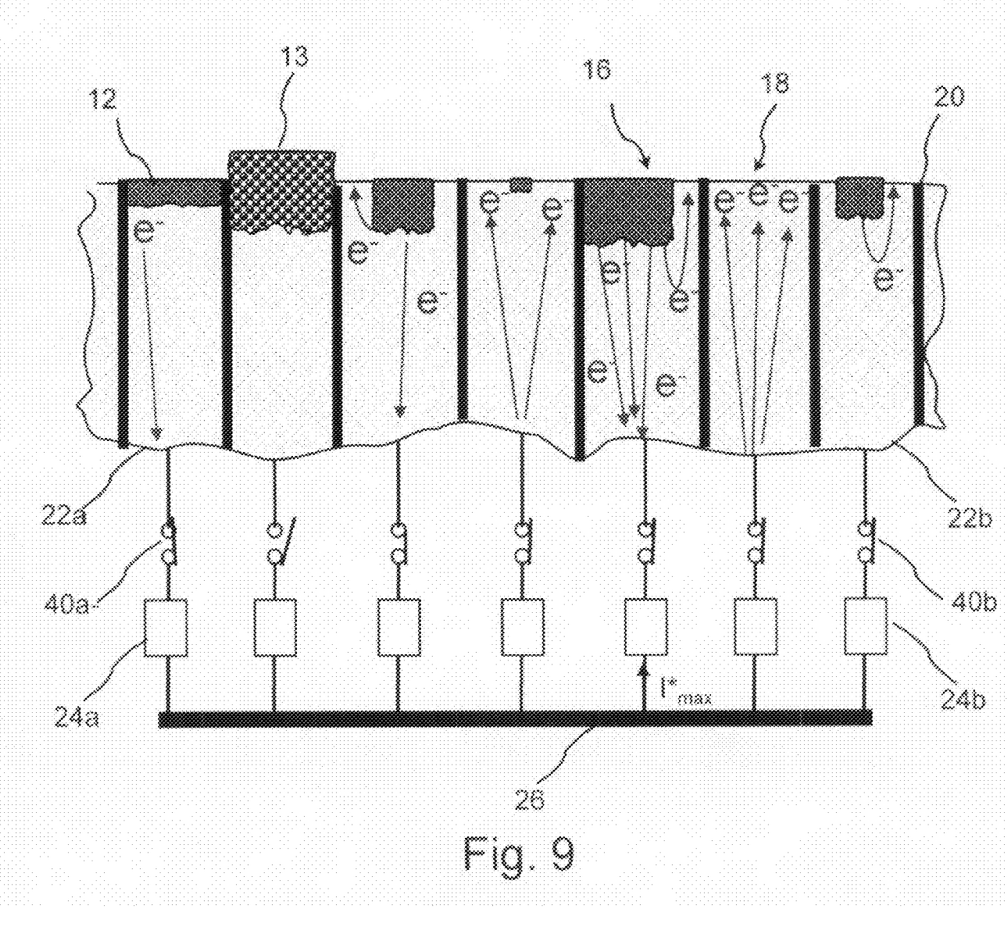
FIG. 9 illustrates that the effect of a bad anodic electrode on the current from the true most corroding electrode can be eliminated, by disconnecting the bad electrode from the coupling joint.

With the switches 40*a* or 40*b*, as shown in FIGS. 3 and 4, the effect of such bad electrode(s) can be easily eliminated—once identified—by disconnecting it (them) from the coupling joint (see FIG. 9).

Figure 10:
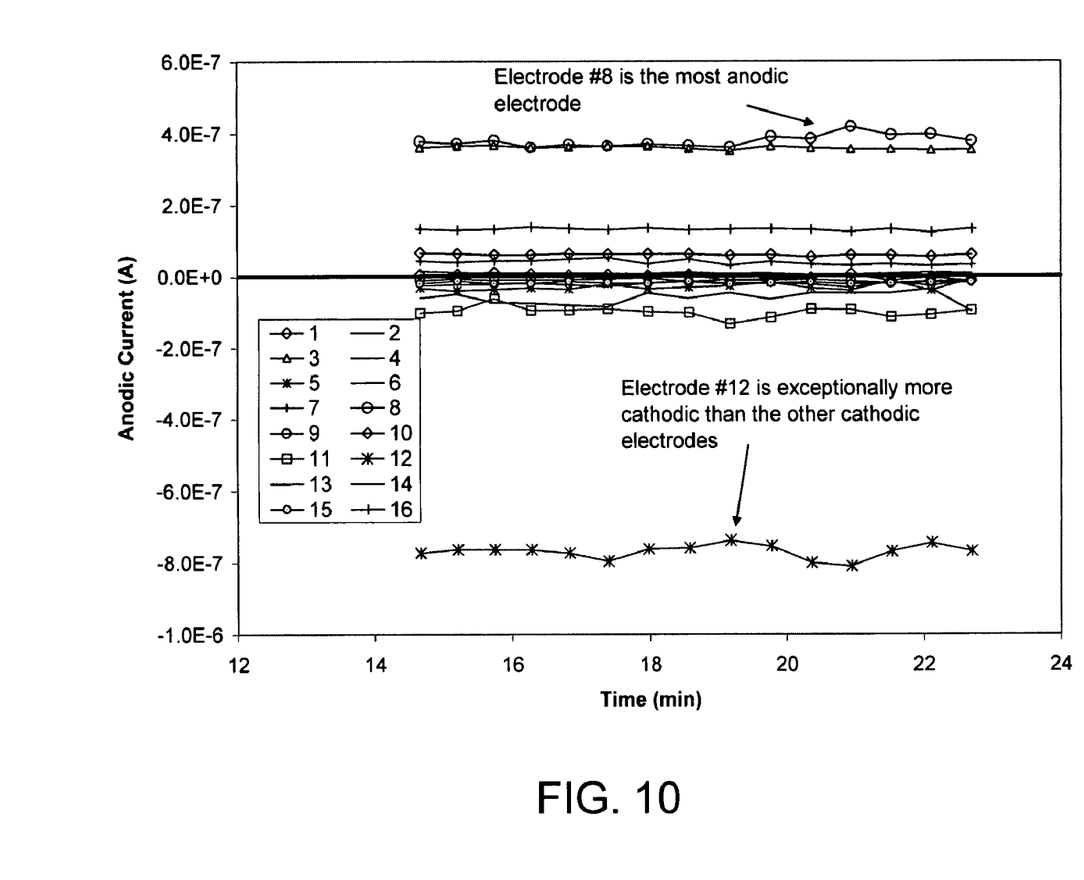
FIG. 10 illustrates a case where one cathodic electrode was a bad electrode statistically; such an electrode should be removed from the coupling joint, to assure reliable measurements.

Similarly, if a small piece of material that is highly catalytic for the reduction reaction of oxygen is stuck on an electrode of the coupled multielectrode sensor probe, this electrode may produce a high cathodic current in an environment containing dissolved oxygen. The cathodic behavior would also drive the corrosion potential of the sensor to be more positive and cause the anodic current flowing through the most corroding electrode to be higher. An example case, observed by the inventors, is provided in FIG. 10. One electrode (Electrode #12) was exceptionally more cathodic than the other electrodes during the measurement. The high anodic current flowing through the most corroding electrodes (Electrode #8) might be due to the effect of the exceptionally cathodic electrode (Electrode #12). Thus, Electrode #12 should be removed from the coupling, using the switches 40*a* or 40*b*.

The behavior of the bad electrode 13 may be identified by statistically analyzing the currents from all the electrodes (both anodic and cathodic electrodes). For an anodic electrode, statistical analysis may also be performed only on those electrodes that are anodic; for a cathodic electrode, the analysis may also be performed only on those electrodes that are cathodic. For example, if an electrode is found to be 3 or 5 times the standard deviation more positive than the mean of all the currents, this electrode is more likely to be a bad anodic electrode. On the other hand, if an electrode is 3 or 5 times the standard deviation more negative than the mean of all the currents, this electrode is more likely to be a bad cathodic electrode.

Two parameters have been introduced by the present inventors to describe the degree of localized corrosion [see X. Sun and L. Yang, "Real-Time Monitoring of Localized and General Corrosion Rates in Simulated Marine Environments Using Coupled Multielectrode Array Sensors," CORROSION/2006, paper no. 06284 (Houston, Tex.: NACE, 2006)] for using coupled multielectrode sensor probes to measure localized corrosion. One such parameter is called localized corrosion rate factor, which is defined as the ratio of the localized corrosion rate (maximum corrosion rate) to the average corrosion rate. It is used to indicate how much higher the maximum localized corrosion rate is than the average corrosion rate, at a given instance in time.

The other parameter is called localized corrosion penetration factor, which is defined as the ratio of the maximum localized corrosion penetration to the average corrosion penetration. The localized corrosion penetration factor is used to indicate how much more the localized corrosion depth is than the average corrosion penetration depth. Because the penetration on each electrode is the integration of the rate, it shows the cumulative degree of localized corrosion over a time period.

Figure 11:
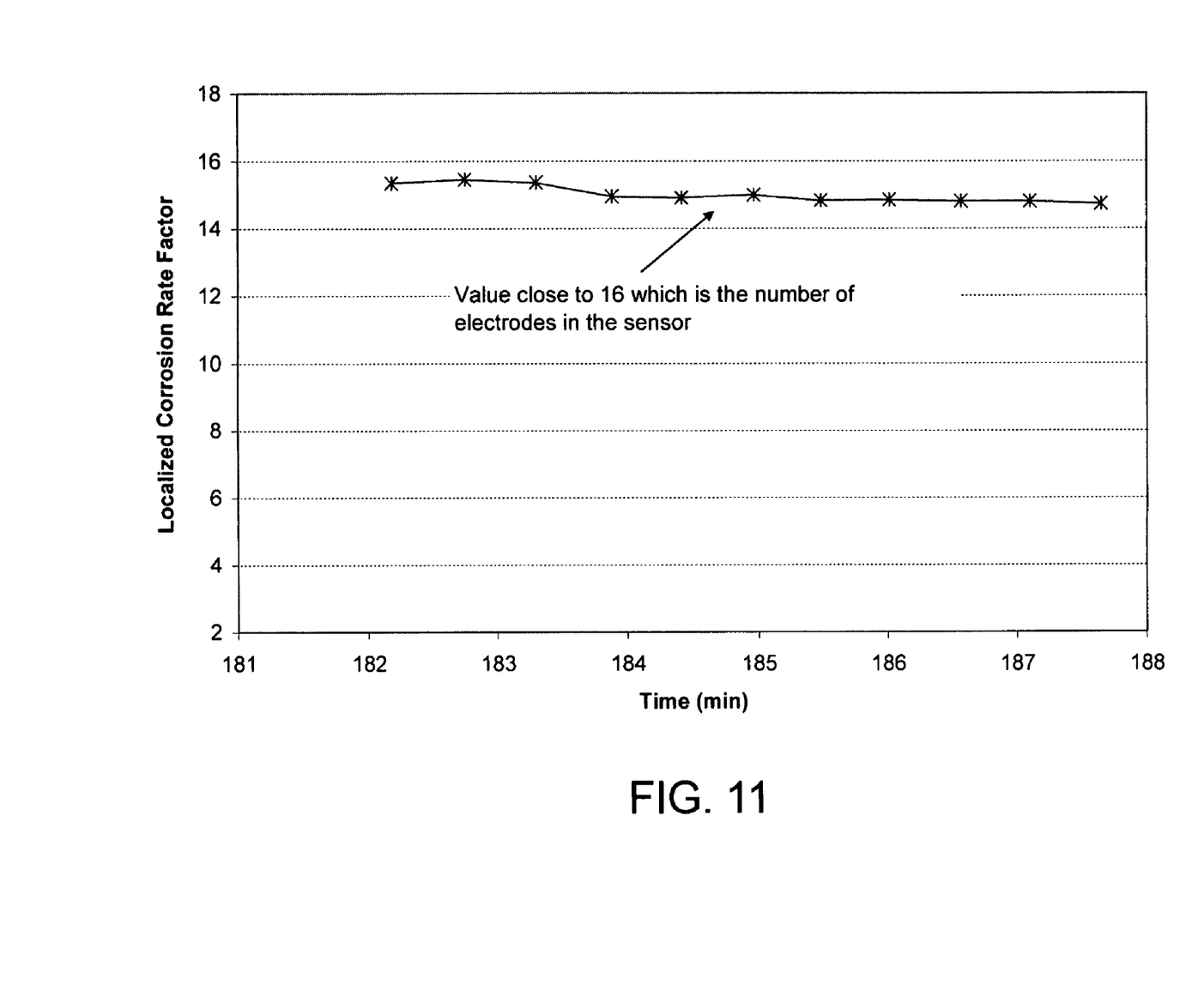
FIG. 11 illustrates the localized corrosion rate factor for the data shown in FIG. 8.

Therefore, if the localized corrosion rate factor—or localized corrosion penetration factor—is close to the number of electrodes in the sensor, there is only one electrode undergoing corrosion. This is an indication of either highly localized corrosion taking place or the presence of a bad anodic electrode. In this case, the most corroding electrode should be removed from the coupling joint. If it is truly due to highly localized corrosion, the localized corrosion rate factor may increase to a high value again, because other electrodes should continue to have severe localized corrosion. If the localized corrosion rate factor does not increase, the disconnected electrode may be considered as the bad electrode. FIG. 11 shows that the localized corrosion rate factor for the data shown in FIG. 8 is, indeed, close to 16, which is the number of the electrodes on the probe, indicating that only one electrode is significantly anodic.

A bad anodic electrode may also be caused by the impurity contained in the metal of the electrode and, thus, the exceptionally high anodic corrosion current may be the true corrosion rate. The removal of this electrode from the coupling may mean the omission of a true exceptionally high signal. However, statistically, if one electrode contains a significant amount of impurity, the other electrodes may also contain a similar amount of impurity. If one electrode is removed from the coupling, localized corrosion should develop rapidly on the other remaining electrodes and one of the these electrodes should reach a similar level of corrosion rate. Therefore, based on the change in corrosion rate before and after the decoupling of the bad electrode, one can confirm whether or not the disconnected electrode is truly a bad electrode.

OTHER EMBODIMENTS

Auto switches or relays may be used in an electronic system, and a computer or a microcontroller may be used to control the auto switches to force all the electrons produced at the most corroding electrode to flow externally and, hence, to obtain the bounding maximum localized corrosion rate. Because localized corrosion rate includes general corrosion rates, the bounding maximum localized corrosion rate is also the bounding corrosion rate for general corrosion. This method may be applied to a probe at a regular interval. That is, during the measurement of localized corrosion rate using the regular method (no anodic electrode is disconnected), some of the anodic electrodes are disconnected at a regular interval (for instance every 10 minutes or every hour) for a short duration (for instance, 2 or 3 minutes), to obtain the bounding value. In this way, the user obtains both the localized corrosion rate and the bounding localized corrosion rate. Alternatively, this method may be applied continually. In this case, the disconnected anodic electrodes need to be connected to the coupling joint at certain intervals for a short duration, so that new anodic electrodes or a new most corroding electrode may be identified. This is because the electrodes under localized corrosion are always under dynamic changes. The anodic electrodes during one time interval may become a cathodic electrode during the next time interval; a cathodic electrode at one interval may also become an anodic electrode during the next time interval. The most corroding electrode at one time interval may become a less corroding electrode and another electrode may become the new most corroding electrode during the next time interval.

Depending upon the purpose, this method may also be applied sparsely, for example, only at the beginning and at the end of measurements.

The criteria regarding which anodic electrodes to disconnect from the coupling joint may also vary under different situations. If a more conservative bounding value is desired, all the anodic electrodes—including those that may become a new anodic electrode after the disconnection of all the anodic electrodes identified during the previous measurement interval—should be removed. In this case, the most corroding electrode is the only electrode that supports the cathodic reactions taking place on the other electrodes that are connected to the coupling joint. If a less conservative bounding value is desired, only the second and/or third most corroding electrode may be removed from the coupling joint. In this case, the most corroding electrode and a few of the other less anodic electrodes remain connected to support the cathodic reactions taking places at all the cathodic sites on the probe. Because the decoupling of the less anodic electrode would cause the rise of the coupling potential, the degree of change in coupling potential may also be used as a criterion to determine the number of anodic electrodes and which anodic electrodes to remove from the coupling joint, for measuring the bounding corrosion rate.

The criteria for identifying the bad electrode may also be based on the corrosion potential of the coupled multielectrode sensor (the coupling potential). If the coupling potential is significantly lower than its usual corrosion potential in a given environment, a bad anodic electrode may exist. On the other hand, if the coupling potential is significantly higher than its usual corrosion potential in a given environment, a bad cathodic electrode may exist. Alternatively, the existence of a bad electrode may be identified or verified by the coupling potential of the coupled multielectrode sensor before and after the extreme electrode is removed from the coupling joint. A large drop in coupling potential after the disconnection verifies that the electrode that was removed was a bad cathodic electrode; a large increase in the corrosion potential of the sensor verifies that the electrode that was removed was a bad anodic electrode.

The criteria for identifying bad electrodes can also be based on the combination of several of the methods mentioned above.

Because the multielectrode sensor probes are expensive, one bad electrode may affect the performance of the probe and make the probe useless. If this electrode can be conveniently disabled, the probe can still be used; one less working electrode would not usually affect the measurements, because a regular coupled multielectrode probe contains many electrodes (from 9 to 25 electrodes). The design shown in FIGS. 3 and 4 may allow a computer program to decouple the bad electrode. With such a program, the user can input the bad electrode identification number and the program will save it into its memory. The program will check this identification number whenever it begins the process of coupling all the electrodes together to start a measurement. If the identification number of an electrode is on this decoupling list, the program will not couple the bad electrode. Therefore, the probe with a permanently bad electrode can still be used.

Although the present invention has been described in detail, it should be understood that various changes, substitutions, and alterations can be made hereto, without departing from the spirit and scope of the invention as defined by the appended claims.

The invention claimed is:

1. A method of using a multielectrode sensor to measure corrosion rate, comprising:
 (a) exposing the sensor to a corrosion environment of interest;
  wherein the sensor has an array of substantially similar metallic electrodes arranged such that each electrode has a surface area operable to be exposed to the corrosion environment, and such that each electrode is electrically insulated from other electrodes;
  wherein each electrode is connected to a coupling joint though a switch that is normally closed and allows the electrode to be disconnected or decoupled from the coupling joint;
 (b) measuring current from each electrode to the coupling joint;
 (c) identifying anodic electrodes based on the current from each electrode;
 (d) decoupling one or more of the anodic electrodes such that a higher percentage of electrons produced on the anodic electrode(s) that remain(s) connected to the coupling joint flow to the coupling joint.

2. The method of claim 1, wherein the anodic electrode that remains connected to the coupling joint is a most corroding electrode.

3. The method of claim 1, wherein the corrosion rate is a bounding rate for localized corrosion.

4. The method of claim 1, wherein the corrosion rate is a bounding rate for general corrosion.

5. The method of claim 1, wherein the current from each electrode to the coupling joint is obtained by measuring the voltage drop across a resistor inserted between the electrode and the coupling joint.

6. The method of claim 1, wherein the current from each electrode to the coupling joint is measured by a zero-resistance ammeter inserted between the electrode and the coupling joint.

7. A method of using a multielectrode sensor to measure corrosion rate, comprising:
 (a) exposing the sensor to a corrosion environment of interest;
  wherein the sensor has an array of substantially similar metallic electrodes arranged such that each electrode has a surface area operable to be exposed to the corrosion environment, and such that each electrode is electrically insulated from other electrodes;

wherein each electrode is connected to a coupling joint though a switch that is normally closed and allows the electrode to be disconnected or decoupled from the coupling joint;

(b) measuring current from each electrode to the coupling joint;

(c) Identifying which electrode is a most corroding electrode and which electrode is a most cathodic electrode and evaluating if the most corroding electrode or the most cathodic electrode is a bad electrode according to a certain criterion;

(d) decoupling the bad electrode, if there is one;

(e) confirming if the decoupled electrode is a truly bad electrode.

8. The method of claim 7, wherein the criterion used to determine whether or not an electrode is a bad electrode is based on how much the current measured from the electrode deviates from the currents measured from the other electrodes on the multielectrode sensor.

* * * * *